United States Patent
Haldeman et al.

(10) Patent No.: US 10,317,323 B2
(45) Date of Patent: Jun. 11, 2019

(54) SCALED ELEMENT TESTING OF WEAR PROTECTION MATERIALS

(71) Applicant: Bell Helicopter Textron Inc., Fort Worth, TX (US)

(72) Inventors: Andrew Paul Haldeman, Forth Worth, TX (US); Ramesh Thiagarajan, Plano, TX (US); Suvankar Mishra, Carrollton, TX (US)

(73) Assignee: Bell Helicopter Textron Inc., Fort Worth, TX (US)

( * ) Notice: Subject to any disclaimer, the term of this patent is extended or adjusted under 35 U.S.C. 154(b) by 0 days.

(21) Appl. No.: 15/782,677

(22) Filed: Oct. 12, 2017

(65) Prior Publication Data

US 2019/0113426 A1    Apr. 18, 2019

(51) Int. Cl.
*G01N 3/00* (2006.01)
*G01N 3/08* (2006.01)
G01N 1/00 (2006.01)
G01N 1/08 (2006.01)

(52) U.S. Cl.
CPC ............... *G01N 3/08* (2013.01); *G01N 1/00* (2013.01); *G01N 1/08* (2013.01); *G01N 3/00* (2013.01); *G01N 2201/00* (2013.01)

(58) Field of Classification Search
CPC ......... G01N 3/08; G01N 1/00; G01N 2201/00
USPC .......................................................... 73/826
See application file for complete search history.

(56) References Cited

U.S. PATENT DOCUMENTS

| 3,559,473 A | * | 2/1971 | Dudderar et al. | ....... G01N 3/04 73/818 |
| 4,563,427 A | * | 1/1986 | Weiss | ..................... G01N 17/00 422/53 |
| 4,706,387 A | * | 11/1987 | Wichorek | ................ G01B 5/30 33/786 |
| 5,528,942 A | * | 6/1996 | Baratta | .................... G01N 3/02 73/818 |

* cited by examiner

*Primary Examiner* — Max H Noori
(74) *Attorney, Agent, or Firm* — Lightfoot & Alford PLLC

(57) ABSTRACT

Systems and methods of operating a test apparatus to simulate testing a production aircraft component include assembling a test assembly having a test specimen and a wear protection material disposed on opposing sides of the test specimen, an outer plate disposed on each side of the test specimen in contact with the wear protection material, and a bolt disposed through the test specimen and the outer plates and applying a preload against the wear protection material. The test assembly is secured in a test machine, and the test machine is operated to provide a predetermined displacement of the test specimen relative to the outer plates at a predetermined frequency at a determined frequency of displacement cycles. The preload, the predetermined displacement, and the predetermined frequency of displacement cycles are determined through finite element analysis of an analytical model of the production component.

20 Claims, 3 Drawing Sheets

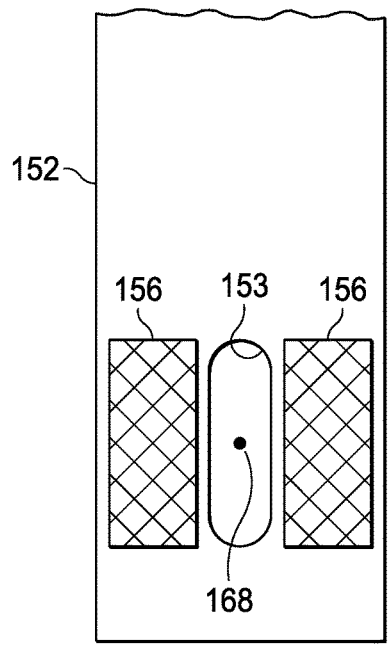
FIG. 3
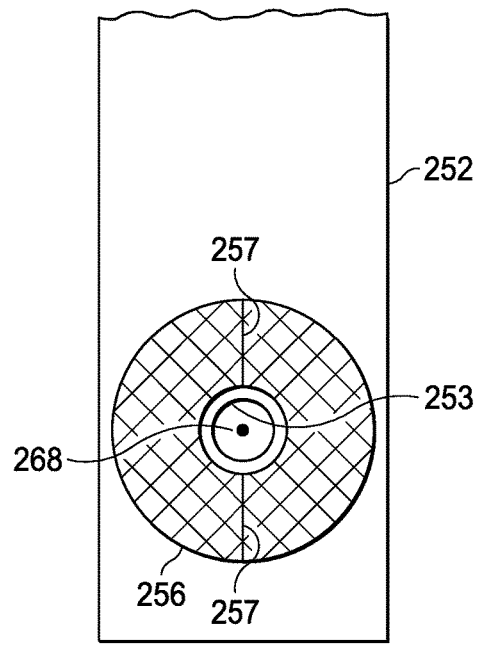
FIG. 4
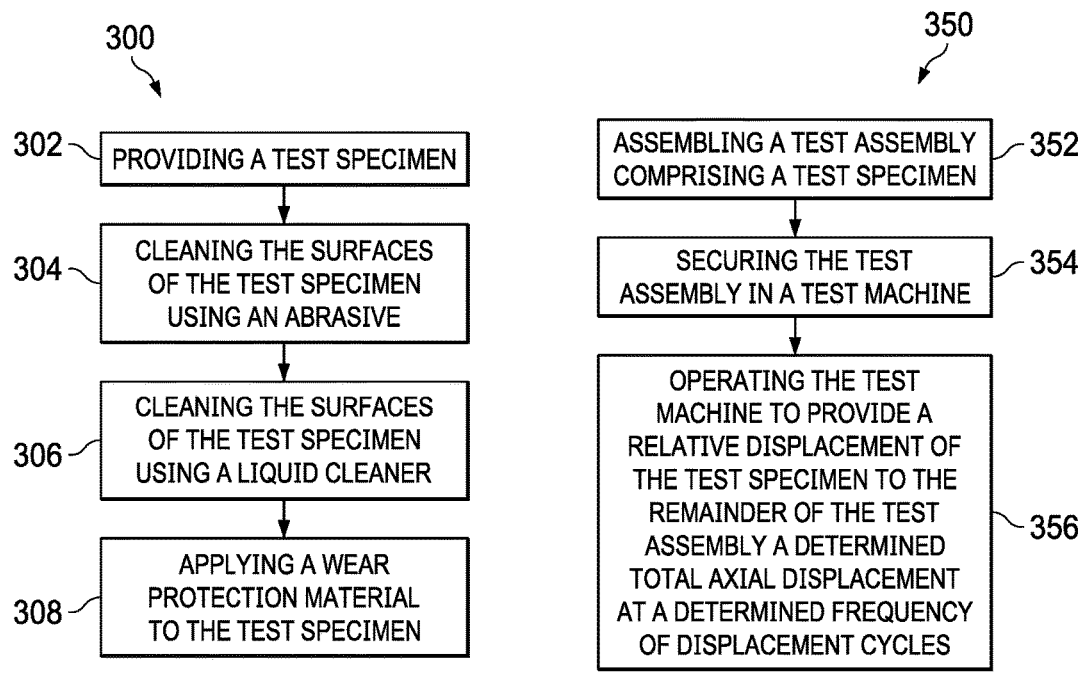
FIG. 5A
FIG. 5B

SCALED ELEMENT TESTING OF WEAR PROTECTION MATERIALS

STATEMENT REGARDING FEDERALLY SPONSORED RESEARCH OR DEVELOPMENT

This invention was made with Government support under Contract No. H1-RCHBACK-16-N00019-16-G-0012, WO: HBAB42. The Government has certain rights in the invention.

CROSS-REFERENCE TO RELATED APPLICATIONS

Not applicable.

REFERENCE TO A MICROFICHE APPENDIX

Not applicable.

BACKGROUND

Testing industrial and/or commercial equipment and/or their components often presents various burdens. In addition to the financial burdens of testing expensive and/or large components, it is often difficult to replicate the loads and vibratory conditions that the components may experience in their intended environment. Specifically, aircraft components often experience excessive velocities, vibrations, and loads when an aircraft is operated and/or in flight that that are difficult and financially burdensome to replicate in a test setting.

SUMMARY

In some embodiments of the disclosure, a test apparatus is disclosed as comprising: a test machine comprising an upper grip and a lower grip; and a test assembly secured within the upper grip and the lower, the test assembly comprising: a test specimen comprising a hole therethrough and a wear protection material disposed on opposing sides of the test specimen and about at least a portion of the hole; an outer plate comprising a hole therethrough and disposed on each side of the test specimen in contact with the wear protection material; and a bolt and at least one nut configured to thread onto the bolt, wherein the bolt is disposed through the holes of the test specimen and the outer plates, and wherein the at least one nut is torqued to provide a preload against the wear protection material and at least a portion of each of the test specimen and the outer plates.

In other embodiments of the disclosure, a method of testing is disclosed as comprising: assembling a test assembly comprising a test specimen comprising a hole therethrough and a wear protection material disposed on opposing sides of the test specimen and about at least a portion of the hole, an outer plate comprising a hole therethrough and disposed on each side of the test specimen in contact with the wear protection material, and a bolt disposed through the holes of the test specimen and the outer plates, and at least one nut configured to thread onto the bolt; applying a preload to the bolt and nut; securing the test assembly in a test machine; and operating the test machine to provide a predetermined displacement of the test specimen relative to the outer plates at a predetermined frequency at a determined frequency of displacement cycles.

BRIEF DESCRIPTION OF THE DRAWINGS

For a more complete understanding of the present disclosure and the advantages thereof, reference is now made to the following brief description, taken in connection with the accompanying drawings and detailed description.

FIG. 3 is a partial orthogonal side view of a test specimen according to an embodiment of the disclosure.

FIG. 4 is a partial orthogonal side view of a test specimen according to an alternative embodiment of the disclosure.

FIG. 5A is a flowchart of a method of preparing a test specimen of a test assembly according to an embodiment of the disclosure.

FIG. 5B is a flowchart of a method of testing a test assembly according to an embodiment of the disclosure.

DETAILED DESCRIPTION

This invention relates generally to a test apparatus and methods for testing materials for wear protection and anti-fretting properties in a lab environment. Because testing full-scale aircraft components presents severe financial constraints and burdens due to the large size and cost of the components, the test apparatus and methods disclosed herein simulate a structural joint of an aircraft component using analytical models of the aircraft and/or the aircraft component and simulates the loads and vibratory conditions realized by the structural joint of the aircraft component using tensile testing machines. The analytical models of the aircraft and/or the aircraft component also includes simulating the preload in the structural joint while allowing for relative motion between the joint surfaces at a frequency that matches high energy rotor system vibrations. Accordingly, the test apparatus and methods disclosed herein provide a realistic environment that produces results of the wear and fretting protection offered by the materials present in the joint, allows the comparison of the durability of wear protection systems, specifically fretting protection, and validates the test parameters developed from the analytical models by employing existing test machinery and/or equipment to execute the tests. Such methods may drastically reduce costs associated with research, development, and testing, while also reducing test schedule durations and test complexity associated with full-scale testing. Further, while the test apparatus and methods disclosed herein were developed to simulate the joints of aircraft components, the test apparatus and methods disclosed herein may also be applicable to the joints of other large industrial and/or commercial components that experience various loads and/or vibratory conditions.

Figure 1:
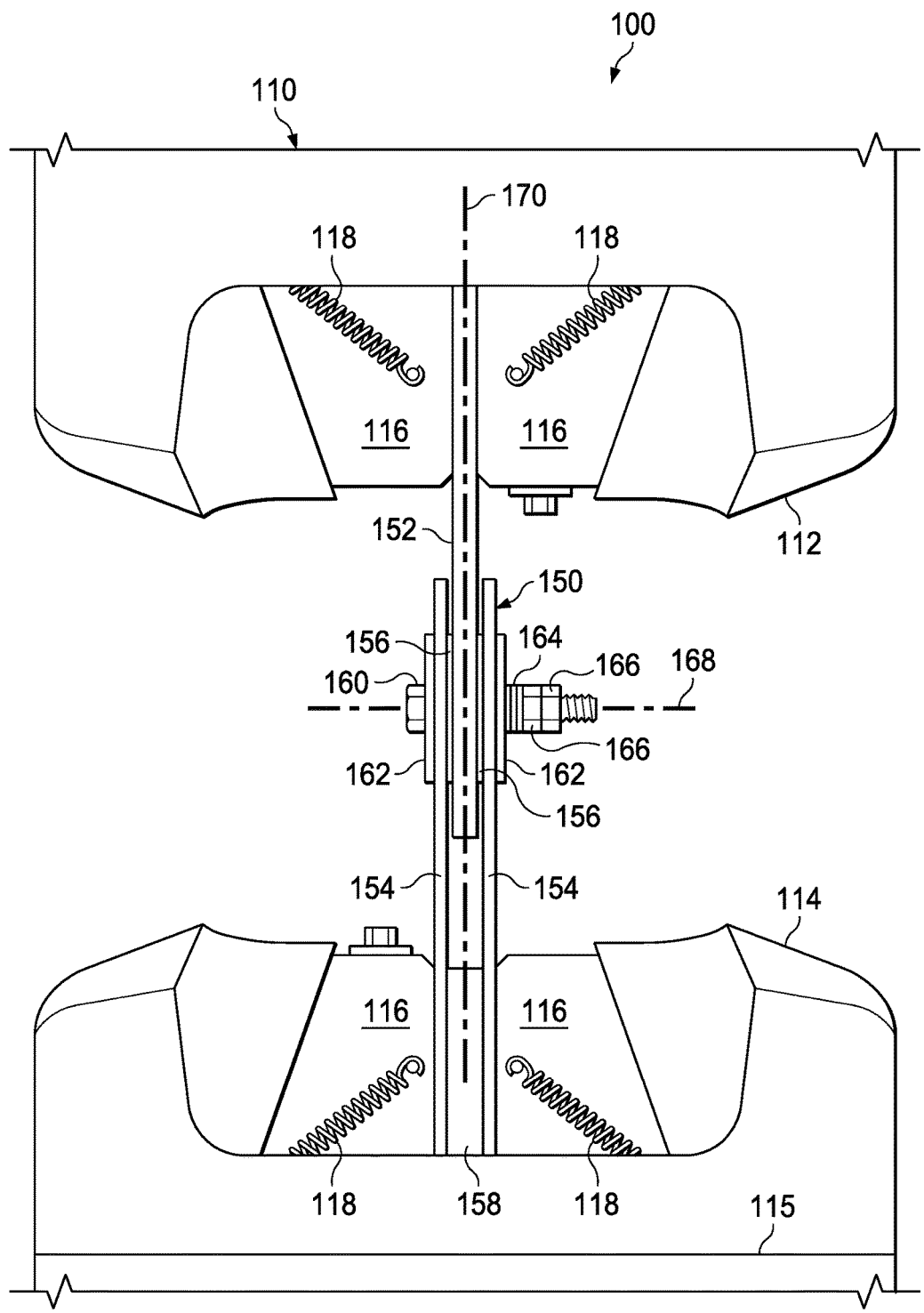
FIG. 1. is a partial orthogonal front view of a test apparatus according to an embodiment of the disclosure.

Referring now to FIG. 1, a partial orthogonal front view of a test apparatus 100 is shown according to an embodiment of the disclosure. The test apparatus 100 generally comprises a test machine 110 and a test assembly 150. The test machine 110 generally comprises a tensile testing machine that comprises an upper grip 112 and a lower grip 114. However, in other embodiments, the test machine 110 may comprise alternative-type test machine comprising a selectively movable member 115 configured to apply an axial displacement, bending moment, and/or torsional rotation to the lower grip 114 and/or the test assembly 150 to further determine wear and/or anti-fretting properties caused by such axial displacement, bending moment, and/or torsional rotation. Each of the grips 112, 114 comprises a pair of jaws 116 for applying pressure to and securely retaining at least a portion of the test assembly 150 during testing between adjacent jaws 116 of each of the upper grip 112 and the lower grip 114. Further, in some embodiments, each of the jaws 116 of the test machine 110 may also comprise a spring 118 which may prevent the jaws 116 from tightening during testing. However, in some embodiments, the springs 118 may retain the jaws 116 in an open position during insertion of a portion of the test assembly 150 into the jaws 116 and/or assembly of the test apparatus 100.

Figure 2:
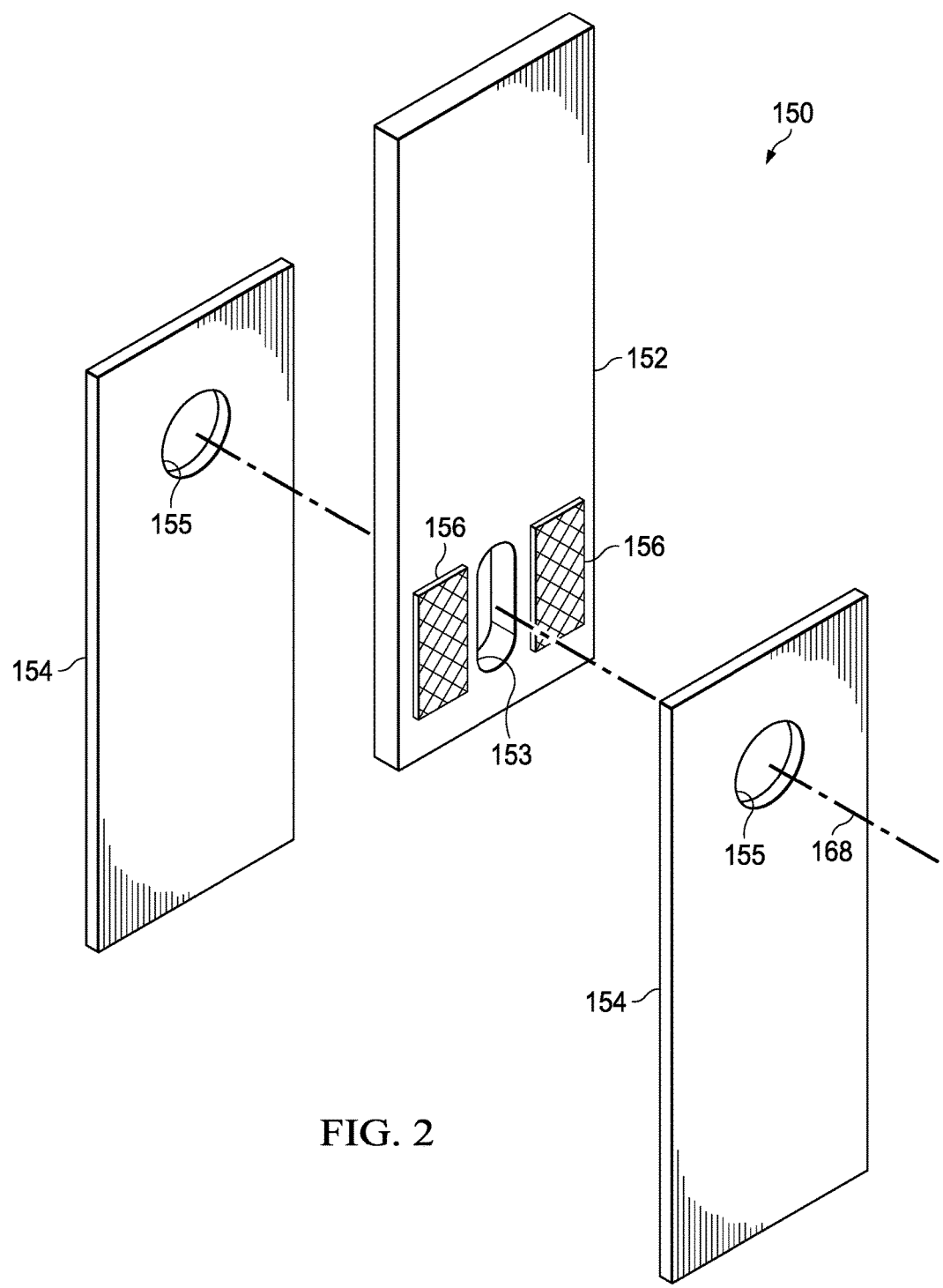
FIG. 2 is a partial oblique exploded view of a test assembly according to an embodiment of the disclosure.

Referring now to FIGS. 1 and 2, test assembly 150 is generally configured to simulate a joint of a production aircraft component that includes wear protection within the joint as a scaled version of the joint without the incumbrances of testing the full-size production aircraft component. For example, in some embodiments, the test assembly 150 may be configured to replicate the metallic joint of an aircraft shear spindle. Accordingly, testing of the test assembly 150 may also be referred to as testing the joint created by the components of the test assembly 150. Because a shear spindle is an intermediate-level consumable component that requires discarding the entire shear spindle when only the wear protection material is damaged, simulating the joint of the shear spindle and/or any other consumable component may allow testing to predict longevity, identify design constraints, and/or streamline the replacement of the wear protection material in the production component at the intermediate level without damaging and requiring disposal of the expensive production component.

To simulate the joint of the production aircraft component, the test assembly 150 generally comprises a test specimen 152 and two outer plates 154 that are assembled in a so-called "lug and clevis" style joint, where the test specimen 152 is disposed between the two, adjacently-disposed parallel outer plates 154. In this embodiment, the test specimen 152 is formed from a 6A1-4V titanium alloy to replicate the material of an aircraft shear spindle. However, in other embodiments, the test specimen 152 may be formed from any composite material, metallic material, and/or any other material that simulates another production aircraft component. The outer plates 154 are generally formed from either a 17-4PH stainless steel or 15-5PH stainless steel. However, in other embodiments, the outer plates 154 may be formed from any other material.

The test assembly 150 also comprises wear protection material 156 applied to the test specimen 152 between the interfacing surfaces of the test specimen 152 and each of the two outer plates 154. In the production aircraft component, the wear protection material comprises Teflon/Dacron. However, in other embodiments, Teflon may be used. However, the wear protection material 156 in the test assembly 150 comprises a first layer of 3M XP2112, double-sided acrylic-based adhesive tape adhered to the test specimen 152, and a second layer of 3M 5453, silicone-based adhesive woven glass cloth tape impregnated with PTFE (polytetrafluoroethylene) adhered to the outer surface of the first layer of double-sided tape. The wear protection material 156 is specifically selected to remain in place while allowing relative movement between the test specimen 152 and the outer plates 154. The wear protection material 156 is also selected to provide the proper thickness of about 0.013 inches while maintaining a tightly-controlled tolerance of about +/−0.002 inches necessary for the production aircraft component. More specifically, the layer of 3M 5453 tape will act as an anti-fretting buffer while the 3M XP2112 double-sided tape acts as a filler to provide the proper thickness. Furthermore, as will be discussed later herein, the wear protection material 156 also allows the test assembly 150 to achieve the proper preload in the joint for testing.

The test assembly 150 also comprises a support plate 158. The support plate 158 may generally be formed from a metallic material and is disposed between the outer plates 154 at an end of the outer plates 154 that interfaces with the jaws 116 of the lower grip 114. The support plate 158 is configured to function as a spacer that allows the jaws 116 of the lower grip 114 to tightly secure the outer plates 154 without substantially deforming and/or collapsing the outer plates 154 inward to maintain the proper geometry between the test specimen 152 and the outer plates 154.

The test assembly 150 also comprises a bolt 160, two outer washers 162 each associated with an outer plate 154, a plurality of smaller washers 164, and two nuts 166 that function as the securing means for the test assembly 150. To simulate the joint of the production aircraft component, the bolt 160 may be selected to comply with National Aerospace Standard 6606, the outer washers 162 and the smaller washers 164 may be selected to comply with National Aerospace Standard 1149, and the nuts 166 may be selected to comply with Military Specification MS21043 or MS 21042. However, it will be appreciated that the bolt 160 may be selected based on the diameter, thread count (threads per inch), thread pitch (metric), and/or strength of the bolt 160 to ensure the required compressive preload is applied to the joint during testing. Additionally, it will be appreciated that the number and/or size of the washers 162, 164 may be selected to provide an equal load distribution to the outer plates 154 and/or the wear protection material 156. Thus, in some embodiments, the test assembly 150 may omit one or more of the outer washers 162 and/or one or more of the plurality of smaller washers 164. In some embodiments, the test assembly 150 may only comprise one nut 166. As will be discussed later herein, the number of outer washers 162, smaller washers 164, and nuts 166 used in the test assembly 150 may be selectively altered to allow the test assembly 150 to achieve the proper preload in the joint and/or load distribution to the wear protection material 156 for testing.

When the test assembly 150 is assembled, the bolt 160 and at least one nut 166 may be used to clamp the test assembly 150 together. The bolt 160 may be inserted through axially-aligned holes 155 in each of the support plates, an axially-slotted hole 153 in the test specimen 152, the outer washers 162, and any smaller washers 164 used in the test assembly 150. As such, the bolt 160 may function to align each of the components of the test assembly 150 clamped together by the bolt 160 and nut 166 along axis 168. Furthermore, to simulate the proper preload in the joint for testing, the bolt 160 and/or the nut 166 may be torqued to a value required to develop the necessary contact pressure on the wear protection material 156 as determined from finite element analysis of the analytical structural model of the production aircraft component to determine the peak contact pressure in the joint, which is then applied to the test assembly 150 as the proper preload. In this embodiment, achieving the proper preload requires 28 ft-lb of torque to be applied to the bolt 160 and/or the nut 166. However, in other embodiments, a different preload may be required as determined via the analytical structural model of the production aircraft component. Still further, it will be appreciated that the addition of an outer, secondary nut 166 may be employed to ensure the proper preload is maintained and prevent a primary, inner nut 166 from backing off and/or loosening along the bolt 160.

In operation, the test specimen 152 is secured by the jaws 116 of the upper grip 112 of the test machine 110, while the outer plates 154 are secured by the jaws 116 of the lower grip 114 of the test machine 110. Alternatively, however, the orientation of the test assembly 150 may be reversed such that the test specimen 152 is secured by the jaws 116 of the lower grip 114, while the outer plates 154 are secured by the jaws 116 of the upper grip 112. One of the grips 112, 114 may remain stationary with respect to the remainder of the test machine 110 while the other grip 112, 114 may move along a longitudinal axis 170. In this embodiment, the upper grip 112 remains stationary, while the lower grip 114 moves along the longitudinal axis 170.

By moving the lower grip 114 longitudinally along axis 170, the test machine 110 controls relative motion between the test specimen 152 and the outer plates 154, which may cause the wear protection material 156 affixed to the test specimen 152 to also move relative to the outer plates 154. The relative motion in the joint of the production aircraft component may also be determined from finite element analysis of the analytical structural model of the production aircraft component to determine the maximum displacement. In this embodiment, the displacement determined from analysis of the production aircraft component is about +/−0.0025 inches. Thus, the test machine 110 may be programmed to apply a total axial displacement along axis 170 of about +/−0.0025 inches between the test specimen 152 and the outer plates 154. The test machine 110 may also be programmed to apply a frequency of displacement cycles as the lower grip 114 oscillates along axis 170. In this embodiment, the frequency of displacement cycles is about 25 Hertz. Accordingly, the motion imparted by the test machine 110 simulates vibration in the production aircraft component by displacing the lower grip 114 along axis 170 the total axially displacement of about +/−0.0025 inches at a frequency of about 25 Hz. However, in other embodiments, the displacement and frequency of displacement cycles may vary for different production aircraft components, and thus may be imparted by the test machine 110 when simulating testing of other test assemblies.

The test machine 110 may also be programmed to test the test assembly 150 by continuously oscillating the test assembly at the proper frequency of 25 Hz at a total axial displacement of about +/−0.0025 inches for a preset testing duration and/or a total number of test cycles. This ensures that the test assembly 150 undergoes enough oscillations to determine the anti-fretting properties of the wear protection material 156 since fretting involves damage induced under load (e.g. preload of test assembly 150) and in the presence of repeated relative motion of interfaced components, as that replicated by the oscillation of the lower grip 114 of the test machine 110 to move the test specimen 152 relative to the outer plates 154.

In some embodiments, the test assembly 150 may also comprise additional components affixed thereto to ascertain specific performance characteristics of the test assembly 150 during testing. For example, a single and/or multiple temperature thermocouples may be affixed to the test specimen 152, the wear protection material 156, and/or other components of the test assembly 150 to monitor temperature, heat generation, and/or temperature profiles across the test specimen 152 and/or the wear protection material 156 caused by friction between the wear protection material 156 and the outer plates 154. Monitoring temperature remains important to maintain a temperature below a maximum operating temperature of the wear protection material 156 and/or adhesives used to adhere the wear protection material 156 to the test specimen 152 to avoid excessively accelerating wear and/or fretting of the wear protection material 156. For example, in some embodiments, the maximum operating temperature of the wear protection material may comprise about 135 degrees Fahrenheit.

Accordingly, the test apparatus 100 is configured to simulate the stress experienced by a joint of a production aircraft component applied through the administered preload of the test assembly 150 and the vibration experienced by the joint of the production aircraft component applied by oscillating the lower grip 114 of the test machine 110 to provide a total axial displacement of about +/−0.0025 inches at a frequency of about 25 Hz to determine the wear and/or anti-fretting properties of the wear protection material 156, which correlates to the wear and/or anti-fretting properties of the Teflon/Dacron anti-fretting material in the joint of the production aircraft component without damaging a production aircraft component. This test assembly 150 and the corresponding method thereby simulates loads, linear and rotational motions, motion frequencies, and material combinations specific to the structural joint in question, and allows testing to be completed in less time and with less cost than a full-scale production aircraft component test.

Thus, test assembly 150 may simulate any joint of a production component prone to wear and/or fretting due to relative motion between interfacing surfaces by using similar and/or exact materials of the interfacing components of the joint and using data from the finite element analysis of the analytical structural model of the production component to determine the required preload to be applied to the test assembly 150, and the total axial displacement and frequency of displacement for the test machine 110 to administer to the test assembly 150. Furthermore, it will be appreciated that in some embodiments, test machine 110 may be configured to apply an axial displacement, bending moment, and/or torsional rotation to the test assembly 150 to further determine wear and/or anti-fretting properties caused by such axial displacement, bending moment, and/or torsional rotation.

Referring now to FIG. 3, a partial orthogonal side view of the test specimen 152 of FIGS. 1 and 2 is shown according to an embodiment of the disclosure. The test specimen 152 generally comprises a rectangular shape comprising a width of about 1.50 inches. The test specimen 152 comprises an axially-slotted hole 153 for receiving the bolt 160 therethrough coaxially along axis 168. The axially-slotted hole 153 comprises a width of about 0.375 inches and a length of about 0.75 inches. The test specimen 152 is generally formed from 6A1-4V titanium alloy. The test specimen 152 also comprises wear protection material 156 affixed to both sides of the test specimen 152. The wear protection material 156 comprises a first layer of 3M) CP2112, double-sided acrylic-based adhesive tape adhered to the test specimen 152, and a second layer of 3M 5453, silicone-based adhesive woven glass cloth tape impregnated with PTFE (polytetrafluoroethylene) adhered to the outer surface of the first layer of double-sided tape. The wear protection material 156 comprises a width of about 0.50 inches and a length of about 0.75 inches. It will be appreciated that the wear protection material 156 comprises substantially the same length as the axially-slotted hole 153. As such, one piece of wear protection material 156 may be affixed adjacently to each of a left and right side of the axially-slotted hole 153 on both sides of the test specimen 152 to simulate the Teflon/Dacron anti-fretting material in the joint of the production aircraft component. This test specimen 152 reflects the placement of the wear protection material 156 for a test specimen 152 and/or production aircraft component comprising an axially-slotted hole 153.

Referring now to FIG. 4, a partial orthogonal side view of a test specimen 252 is shown according to an alternative embodiment of the disclosure. Test specimen 252 is substantially similar to test specimen 152 and may be used in test assembly 150; however, test specimen 252 reflects the placement of the wear protection material 256 for a test specimen 252 and/or production aircraft component comprising a round hole 253. The test specimen 252 generally comprises a rectangular shape comprising a width of about 1.50 inches. The round hole 253 comprises a diameter of about 0.375 inches. The test specimen 252 is also generally formed from 6Al-4V titanium alloy. The test specimen 252 also comprises wear protection material 256 affixed to both sides of the test specimen 252. The wear protection material 256 also comprises a first layer of 3M XP2112, double-sided acrylic-based adhesive tape adhered to the test specimen 152, and a second layer of 3M 5453, silicone-based adhesive woven glass cloth tape impregnated with PTFE (polytetrafluoroethylene) adhered to the outer surface of the first layer of double-sided tape. The wear protection material 256 comprises an outer diameter of about 1.125 inches and an inner diameter of about 0.50 inches. It will be appreciated that one piece of wear protection material 256 may be affixed coaxially with axis 268 about the hole 253 on both sides of the test specimen 252 to simulate the Teflon/Dacron anti-fretting material in the joint of the production aircraft component. However, in some embodiments, the wear protection material 256 may comprise two separate pieces spliced at butt joint 257 on both sides of the test specimen 252.

Referring now to FIG. 5A, a flowchart of a method 300 of preparing a test specimen 152, 252 of a test assembly 150 is shown according to an embodiment of the disclosure. The method 300 may begin at block 302 by providing a test specimen 152, 252. In some embodiments, the test specimen 152, 252 may be formed from 6Al-4V titanium alloy. The method 300 may continue at block 302 by cleaning the surfaces of the test specimen 152, 252 using an abrasive. In some embodiments, the abrasive may comprise an abrasive paper comprising a 220 grit. However, in some embodiments, the abrasive may comprise an abrasive paper comprising a grit finer than 220 grit. In yet other embodiments, cleaning the surfaces of the test specimen 152, 252 using an abrasive may comprise a first step of using a 220-grit abrasive paper and at least one subsequent step of using finer than 220 grit abrasive paper. The method 300 may continue at block 306 by cleaning the surfaces of the test specimen 152, 252 using a liquid cleaner. In some embodiments, the liquid cleaner may comprise Methyl Ethyl Ketone (MEK), acetone, isopropyl alcohol, and/or any other liquid cleaner. The method 300 may conclude at block 308 by applying a wear protection material 156 to the test specimen 152, 252. In some embodiments, applying the wear protection material 156 comprises applying a first layer of 3M XP2112, double-sided acrylic-based adhesive tape adhered to the test specimen 152 and a second layer of 3M 5453, silicone-based adhesive woven glass cloth tape impregnated with PTFE (polytetrafluoroethylene) to the outer surface of the first layer.

Referring now to FIG. 5B, a flowchart of a method 350 of testing a test assembly 150 is shown according to an embodiment of the disclosure. The method 350 may continue from block 308 of method 300 of FIG. 5A and begin at block 352 by assembling a test assembly 150 comprising a test specimen 152, 252. In some embodiments, the test assembly 150 may be assembled by applying a preload to a bolt 160 and/or nut 166 determined from finite element analysis of the analytical structural model of the production aircraft component to determine the peak contact pressure in the joint, which is then applied to the test assembly 150 as the preload. In some embodiments, the preload requires 28 ft-lb of torque to be applied to the bolt 160 and/or the nut 166. The method 350 may continue at block 354 by securing the test assembly 150 in a test machine 110. This may be accomplished by securing the test assembly 150 in jaws 116 of an upper grip 112 and a lower grip 114 of a test machine 110. The method 350 may conclude at block 356 by operating the test machine 110 to provide a relative displacement of the test specimen 152, 252 to the remainder of the test assembly 150 a determined total axial displacement at a determined frequency of displacement cycles. This may also be referred to as testing the test assembly 150. In some embodiments, the determined total axial displacement and the determined frequency of displacement cycles may be determined from finite element analysis of the analytical structural model of the production aircraft component to determine the maximum displacement and the frequency to simulate the vibration in the production aircraft component. In some embodiments, the total axial displacement along axis 170 is about +/−0.0025 inches, and the frequency of displacement cycles is about 25 Hertz.

In some embodiments, the test machine 110 may be operated to provide a relative displacement of the test specimen 152, 252, to the remainder of the test assembly 150 a determined total axial displacement at a determined frequency of displacement cycles for a predetermined time duration. However, in some embodiments, the method 350 may further comprise performing a torque check every hour of testing. A torque check requires that if rotation of the nut 166 and/or nuts 166 is observed and/or a reduction in the preload, the nut 166 and/or nuts 166 may be retorqued to the required torque value until no rotation of the nut 166 and/or nuts 166 is observed. The torque is considered stabilized when two consecutive torque checks show no loss in torque (i.e. no rotation of the nut 166 and/or nuts 166 with the proper torque of 28 ft-lb). Accordingly, upon torque stabilization, the torque check frequency can be doubled. (e.g. every 2 hours). Furthermore, it will be appreciated that the total duration of testing may be determined based on torque stabilization results.

At least one embodiment is disclosed, and variations, combinations, and/or modifications of the embodiment(s) and/or features of the embodiment(s) made by a person having ordinary skill in the art are within the scope of this disclosure. Alternative embodiments that result from combining, integrating, and/or omitting features of the embodiment(s) are also within the scope of this disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 95 percent, 98 percent, 99 percent, or 100 percent. Moreover, any numerical range defined by two R numbers as defined in the above is also specifically disclosed.

Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present invention. Also, the phrases "at least one of A, B, and C" and "A and/or B and/or C" should each be interpreted to include only A, only B, only C, or any combination of A, B, and C.

What is claimed is:

1. A test apparatus, comprising:
   a test machine comprising an upper grip and a lower grip; and
   a test assembly secured within the upper grip and the lower, the test assembly comprising:
      a test specimen comprising a hole therethrough and a wear protection material disposed on opposing sides of the test specimen and about at least a portion of the hole;
      outer plates comprising a hole therethrough and disposed on each side of the test specimen in contact with the wear protection material; and
      a bolt and at least one nut configured to thread onto the bolt, wherein the bolt is disposed through the holes of the test specimen and the outer plates, and wherein the at least one nut is torqued to provide a preload against the wear protection material and at least a portion of each of the test specimen and the outer plates.

2. The test apparatus of claim 1, wherein the wear protection material comprises a layer of silicone-based adhesive woven glass cloth tape impregnated with PTFE (polytetrafluoroethylene) adhered to the test specimen.

3. The test apparatus of claim 1, wherein the wear protection material comprises a first layer of double-sided acrylic-based adhesive tape adhered to the test specimen and a second layer of silicone-based adhesive woven glass cloth tape impregnated with PTFE (polytetrafluoroethylene) adhered to the first layer.

4. The test apparatus of claim 3, wherein the wear protection material is selected to provide a thickness of about 0.013 inches and maintain a tolerance of about +/−0.002 inches.

5. The test apparatus of claim 1, wherein the hole in the test specimen comprises at least one of a round hole and an axially-slotted hole.

6. The test apparatus of claim 5, wherein materials of the test specimen and the outer plates are selected to simulate the materials of a production component.

7. The test apparatus of claim 6, wherein the test specimen is secured in the upper grip of the test machine and remains stationary, and wherein the outer plates and a support plate disposed between the outer plates are secured in the lower grip configured to oscillate to provide a predetermined displacement of the test specimen relative to the outer plates at a predetermined frequency of displacement cycles.

8. The test apparatus of claim 7, wherein the test machine is operated to apply the predetermined displacement at the predetermined frequency of displacement cycles for a predetermined time duration.

9. The test apparatus of claim 8, wherein the preload, the predetermined displacement, and the predetermined frequency of displacement cycles are determined through finite element analysis of an analytical model of the production component.

10. A method of testing, comprising:
    assembling a test assembly comprising a test specimen comprising a hole therethrough and a wear protection material disposed on opposing sides of the test specimen and about at least a portion of the hole, an outer plate comprising a hole therethrough and disposed on each side of the test specimen in contact with the wear protection material, and a bolt disposed through the holes of the test specimen and the outer plates, and at least one nut configured to thread onto the bolt;
    applying a preload to the bolt and nut by applying torque to the nut;
    securing the test assembly in a test machine; and
    operating the test machine to provide a predetermined displacement of the test specimen relative to the outer plates at a predetermined frequency of displacement cycles.

11. The method of claim 10, further comprising: determining the preload, the predetermined displacement, and the predetermined frequency of displacement cycles through finite element analysis of an analytical model of a production component.

12. The method of claim 10, further comprising: operating the test machine for a predetermined time duration.

13. The method of claim 12, further comprising: performing a torque check of the preload for a predetermined interval of the time duration.

14. The method of claim 13, wherein the performing the torque check of the preload comprises retorquing the bolt and nut to the preload in response to a reduction in the preload.

15. The method of claim 14, wherein the preload is stabilized when two consecutive torque checks show no loss in preload.

16. The method of claim 10, wherein materials of the test specimen and the outer plates are selected to simulate the materials of a production component.

17. The method of claim 16, further comprising: prior to assembling the test assembly, cleaning the test specimen using an abrasive comprising an abrasive comprising at least one of a 220-grit abrasive and a finer than 220-grit abrasive; and
    after cleaning the test specimen using the abrasive, cleaning the test specimen using a liquid cleaner comprising at least one of Methyl Ethyl Ketone (MEK), acetone, and isopropyl alcohol.

18. The method of claim 17, further comprising: after cleaning the test specimen using the liquid cleaner, applying the wear protection material to the test specimen.

19. The method of claim 18, wherein applying the wear protection material comprises applying a layer of silicone-based adhesive woven glass cloth tape impregnated with PTFE (polytetrafluoroethylene) to the test specimen.

20. The method of claim 18, wherein applying the wear protection material comprises applying a first layer of double-sided acrylic-based adhesive tape to the test specimen and a second layer of silicone-based adhesive woven glass cloth tape impregnated with PTFE (polytetrafluoroethylene) to the first layer.

* * * * *